United States Patent [19]

Menge et al.

[11] 4,016,280

[45] Apr. 5, 1977

[54] 4,4-DIARYLPIPERIDINE COMPOSITIONS AND USE

[75] Inventors: Heinz Günter Menge, Constance; Josef Klosa, Berlin, both of Germany

[73] Assignee: Byk Gulden Lomberg Chemische Fabrik GmbH, Germany

[22] Filed: May 13, 1975

[21] Appl. No.: 576,973

Related U.S. Application Data

[60] Division of Ser. No. 455,041, March 26, 1974, which is a continuation-in-part of Ser. No. 55,957, July 17, 1970, abandoned.

[30] Foreign Application Priority Data

July 17, 1969  Germany .......................... 1936452

[52] U.S. Cl. .............................................. 424/267
[51] Int. Cl.² ...................................... A61K 31/445
[58] Field of Search .................................. 424/267

[56] References Cited

UNITED STATES PATENTS 3,468,893  9/1969  Mizzoni ............................. 260/293

OTHER PUBLICATIONS

Marshall–Brit. J. Pharmacology, vol. 10 (1955) pp. 270–278.

*Primary Examiner*—Sam Rosen
*Attorney, Agent, or Firm*—Berman, Aisenberg & Platt

[57] ABSTRACT

4,4-Diarylpiperidine compounds, preferably 4,4-diphenylpiperidine which are substituted or unsubstituted in the 1-position of the piperidine nucleus, such as 1-(lower alkyl)-4,4-diphenylpiperidines, 1-(lower alkyl)-4-phenyl-4-tolylpiperidines, and their substantially non-toxic, pharmaceutically-acceptable acid addition salts, are highly effective central nervous system (CNS) stimulants which are superior to known amphetamine-type stimulants. A novel and highly advantageous process of making such 4,4-diarylpiperidine compounds comprises reacting a 4-aryl-4-hydroxypiperidine compound which may be substituted in its 3-position by an aroyl group, with an aromatic hydrocarbon, in particular with benzene, in the presence of a Friedel-Crafts-type catalyst.

25 Claims, No Drawings

4,4-DIARYLPIPERIDINE COMPOSITIONS AND USE

CROSS-REFERENCE TO RELATED APPLICATIONS

This application is a division of our pending application Ser. No. 455,041, filed Mar. 26, 1974, which is a continuation-in-part of our abandoned patent application Ser. No. 55,957, filed July 17, 1970.

BACKGROUND OF THE INVENTION

1. Field of the Invention

The present invention relates (a) to substituted piperidine compounds and more particularly to 4,4-diarylpiperidines which are or are not substituted in the 1-position of the piperidine nucleus and/or in at least one of the aryl rings, (b) to an advantageous process for making such compounds, (c) to pharmaceutical compositions containing same, and (d) to methods of using such compositions in therapy for their central nervous system stimulating effect.

2. Description of the Prior Art

1-Methyl-4,4-diphenylpiperidine and 1-(secondary butyl)-4,4-diphenylpiperidine are mentioned in Brit. J. Pharmacol., Vol. 10, pages 270 to 278 (1955), by Marshall, the disclosure thereof is incorporated herein (in its entirety) by reference. Both compounds are tested by Marshall for their antihistaminic activity using the technique of Schild [Brit. J. Pharmacol. (1947), Vol. 2, pages 189 to 206]. From inspection of Table II (pages 272 and 273) and of FIG. 3 (page 275) of the Marshall citation, it is evident to the pharmacologist skilled in the art that both compounds, 1-methyl-4,4-diphenylpiperidine and 1-(secondary butyl)-4,4,-diphenylpiperidine are devoid of any therapeutically utilizable antihistaminic activity.

N. Sperber et al. describe [Journ. Am. Chem. Soc., Vol. 75, pages 1122 to 1125 (1953)]processes for preparing 1-methyl-4,4-diphenylpiperidine. According to one process diphenyl methane is reacted with 2-dimethylaminoethyl chloride to produce 3,3-diphenyl-N,N,N',N'-tetramethyl-1,5-pentanediamine. On ring closure, 1-methyl-4,4-diphenylpiperidine is obtained in a low yield.

According to a second process disclosed by Sperber (loc. cit.) diphenylmethane is reacted with 2-bromoethyl ethyl ether to yield 3,3-diphenyl-1-ethoxypropane. Alkylation of 3,3-diphenyl-1-ethoxypropane with 2-dimethylaminoethyl chloride yielded 5-ethoxy-3,3-diphenyl-N,N-dimethylamine; cleavage of the ethoxy group gave 5-hydroxy-3,3-diphenyl-N,N-dimethylamine hydrobromide, which was reacted with thionyl chloride to give 4,4-diphenyl-1,1-dimethylpiperidinium chloride, from which sublimation in vacuo yielded 1-methyl-4,4-diphenylpiperidine. This synthesis includes 5 reaction steps and provides an overall maximum yield of about 23 percent of theory. The availability of this synthesis for the preparation of homologues of 1-methyl-4,4-diphenylpiperidine, e.g. of 1-ethyl-4,4-diphenyl-piperidine or 1-isopropyl-4,4-diphenylpiperidine has to be regarded as doubtful.

Sperber refers to L. O. Randall and G. Lehmann, J. Pharmacol. Exp. Therap. Vol 93, pages 314 to 328 (1948), who evaluated 1-methyl-4,4-diphenylpiperidine along with several other series of compounds, and found it to be devoid of analgesic activity [See Sperber (loc. cit.), footnote 5 on page 1122].

With regard to the process for the preparation of 4,4-diarylpiperidines hereinafter described and claimed and its status as a non-analogous process in view of the background of the prior art, the disclosure of the article of N. G. Sidorova et al., J. Gen. Chem. USSR, Vol. 7, pages 1830 to 1833 (1957), is incorporated herein by reference.

In U.S. Pat. No. 3,468,893 Mizzoni discloses the preparation of 1-substituted diphenylazacycloalkenes, which compounds are supposed to be useful as hypotensive agents. The general formula given by Mizzoni encompasses an immense number of substituted azacycloalkenes of which the alkyleneimino ring may represent piperidino, pyrrolidino, 1,5-, 1,6- or 2,5-hexyleneimino, 1,5-, 1,6-, 1,7- or 2,6-heptyleneimino or 1,8-, 3,6- or 3,7-octyleneimino. In Example 13 of the patent, inter alia, the compounds 1-(2-hydroxyor chloro-ethyl)-4,4-diphenylpiperidine are mentioned but apparently no 4,4-diphenylpiperidine was actually prepared. In fact, the synthetic methods discussed in the patent for the preparation of the various 1-substituted diphenylazacycloalkenes either could not be adapted for the preparation of 4,4-diphenylpiperidines, or starting materials, such as 2,2-diphenylglutaric acid mononitrile ethyl ester, are unknown and unavailable.

SUMMARY OF THE INVENTION

It is one object of the present invention to provide a novel and advantageous process of producing 4,4-diphenylpiperidine compounds.

Another object of the present invention is to provide novel 4,4-diphenylpiperidine compounds with valuable properties.

A further object of the present invention is to provide novel and highly effective pharmaceutical compositions containing 4,4-diphenylpiperidine compounds.

Still another object of the present invention is to provide a method of using such compositions in therapy.

Other objects of the present invention and advantageous features thereof will become apparent as the description proceeds.

A. NOVEL PROCESS OF PRODUCING 4,4-DIPHENYLPIPERIDINES

The novel and advantageous process of producing 4,4-diphenylpiperidine compounds comprises condensing 4-hydroxy-4-arylpiperidines of formula II, which may contain an aroyl group in the 3-position of the piperidine nucleus, with an aromatic hydrocarbon, particularly benzene or toluene, in the presence of a Friedel-Crafts-type catalyst, preferably in the presence of anhydrous aluminum chloride or ferric chloride, according to the following equation:

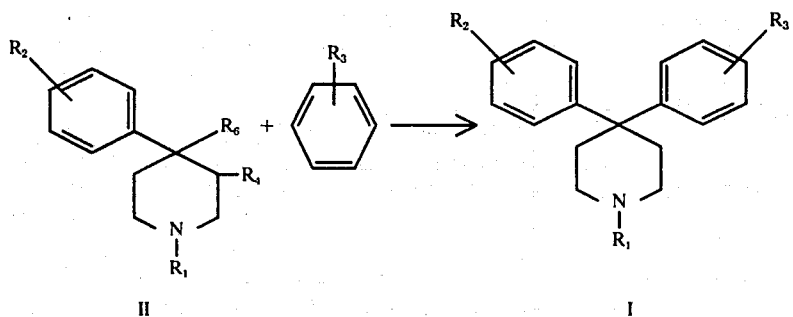

wherein
R₁ is a hydrogen atom (—H), straight-chain or branched alkyl with 1 to 6 carbon atoms, nuclearly-substituted or unsubstituted phen(lower)alkyl, hydroxy(lower)alkyl, (lower)alkyl[carbonyl or oxo](lower)alkyl, (lower)alkoxy-(lower)alkyl, nuclearly-substituted or unsubstituted phenoxy(lower)alkyl, nuclearly-substituted or unsubstituted phenyl[carbonyl or oxo](lower)alkyl, nuclearly-substituted or unsubstituted phen(lower)alkoxy(-lower)alkyl; wherein each designation "lower" denotes a carbon skeleton having from 1 to 4 carbon atoms; any substituent of nuclearly-substituted phen(lower)alkyl, phenoxy(lower)alkyl, phen(-lower)alkoxy(lower)alkyl or phenyl[carbonyl or oxo](lower)alkyl being a halogen atom having an atomic number from 9 to 35, in particular fluorine or chlorine;

each of $R_2$ and $R_3$ is, independently, a hydrogen atom (—H) or alkyl with 1 to 4 carbon atoms;

$R_4$ is a hydrogen atom (—H) or the

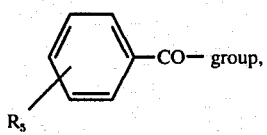

$R_5$ has one of the meanings ascribed to $R_2$; and
$R_6$ is halo, e.g. chloro, fluoro or bromo, or, preferably, —OH.

The term "lower alkyl" comprises, e.g., methyl, ethyl, n-propyl, n-butyl; the term phen(lower)alkyl comprises, e.g., benzyl, phenethyl and 1-phenyl-2-propyl; the term (lower)alkoxy(lower)alkyl comprises, e.g., methoxymethyl, methoxy-n-propyl, n-propoxy-methyl and n-propoxy-n-propyl. In the same manner the scope of each substituent $R_1$ is determined.

In a preferred embodiment 4-hydroxy-4-arylpiperidines of formula II are reacted with benzene [$R_3$ denotes a hydrogen atom (—H) and the substituents $R_1$, $R_2$ and $R_4$ have their previously-ascribed meanings] according to the following scheme to form the preferred compounds of formula Ia:

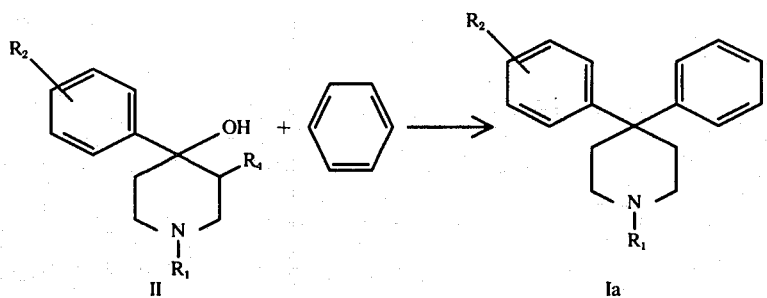

The most preferred compounds which can be prepared according to the above given schemata with Friedel-Crafts-type catalysts can be denoted by the following formula I*,

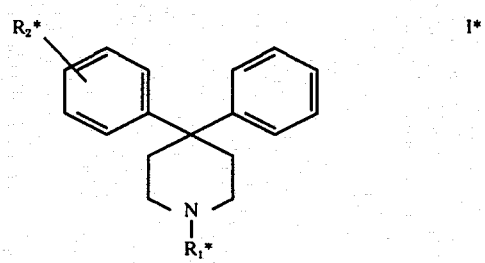

wherein
$R_1^*$ is a hydrogen atom (—H), methyl, ethyl, n-propyl, isopropyl, n-butyl, secondary butyl, tertiary butyl, n-amyl, isoamyl, n-hexyl, benzyl, p-fluorobenzyl, p-chlorobenzyl, phenethyl, 1-phenyl-2-propyl, methoxyethyl, methoxy-n-propyl, ethoxyethyl, acetonyl, phenoxymethyl, phenoxyethyl, benzyloxymethyl, benzyloxyethyl, benzoylmethyl, 2-benzoylethyl, 3-benzoylpropyl, 3-(p-fluorobenzoyl)-propyl and 3-(p-chlorobenzoyl)propyl and
$R_2^*$ denotes a hydrogen atom (—H) or alkyl with from 1 to 4 carbon atoms; $R_2^*$ is preferably —H.

As in the reaction schemata delineated above $R_4$ is, e.g., the

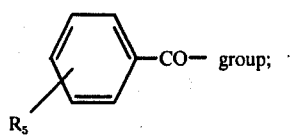
-CO— group;

in one variant the starting material for the preparation of compounds I, Ia and I* is selected from the group of 4-aryl-4-hydroxy-3-aroylpiperidines of the formula IIa and the reaction proceeds as follows:

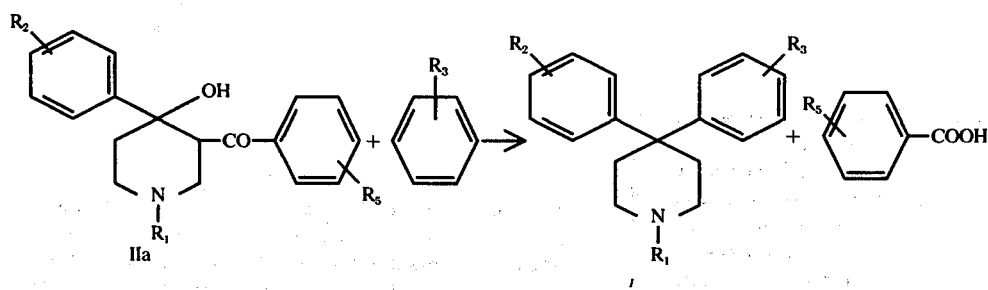

In this scheme $R_1$, $R_2$, $R_3$ and $R_5$ have their previously-ascribed meanings and $R_3$ preferably denotes a hydrogen atom (—H).

The 4,4-diphenylpiperidine compounds of formulae I, Ia and I*, are also obtained when replacing the 4-hydroxy-4-arylpiperidines of formula II or the 4-hydroxy-4-aryl-3-aroylpiperidines of formula IIa by corresponding compounds in which the 4-hydroxyl group is replaced by another functional reactive group, such as a halogen, in particular a chlorine atom. However, use of hydroxyl compounds as reactants has proved to be especially suitable for carrying out the novel process according to the present invention.

The process as described hereinabove is novel and chemically unobvious. It could not be foreseen that said reactions would proceed in such a simple manner and quite rapidly as well as with a yield of between 60 and 90% and that the reaction products would be substantially free from by-products.

It is especially surprising that the benzoyl group is split off during the reaction when proceeding according to schema IIa → I because said benzoyl group is present in the starting material in the form of a reactive keto group capable of reaction in the presence of Friedel-Crafts catalysts. It is to be expected that intramolecular condensations will take place thereby. Surprisingly, however, such intramolecular condensation reactions do not occur.

STARTING MATERIAL

The starting materials of formulae II and IIa, as they are required for carrying out the process of this invention, are known or produced in a manner known per se.

For instance, the compounds of formula II are obtained by reacting 4-piperidones with phenyl lithium or with Grignard compounds of halogeno benzenes. The preparation of compounds of the formula II wherein $R_4$ denotes a hydrogen atom is described in detail in U.S. Pat. No. 3,438,991; in Danish Pat. No. 60,592; in Dansk. Tidsskr. Farm., Vol. 17, pages 173 to 182 (1943); in J. Org. Chem., Vol. 12, pages 885 to 893 (1947); ibid., pages 904 to 910; in German Pat. No. 818,803; and in J.A.C.S., Vol. 71, page 901 (1949).

The compounds of formula IIa are obtained by reacting acetophenones with paraformaldehyde and amine salts. The preparation of compounds of formula IIa is described in detail in Chemical Abstracts, Vol. 31, 2592 (1937); in Ber. dtsch. chem. Ges., Vol. 75, page 49 (1942); in German Pat. No. 820,141 and in French Pat. No. 1,600,4449.

REACTION

The starting materials of the formulae II or IIa are dissolved or suspended in an aromatic hydrocarbon having the formula

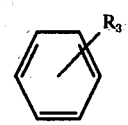

wherein $R_3$ has its above-ascribed meaning. In the preferred embodiment anhydrous benzene or toluene is used as the aromatic hydrocarbon. The Friedel-Crafts catalyst preferably anhydrous aluminum chloride or ferric chloride, or another Lewis acid, such as antimony pentachloride, tin tetrachloride or zinc chloride, is used in at least stoichiometric amounts in relation to compounds II and IIa, e.g. in a molar ratio of catalyst; II or IIa of from about 6:1 to 2:1, preferably of from about 5:1 to 4:1, whereas the aromatic hydrocarbon having the formula

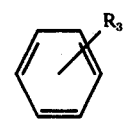

wherein $R_3$ has its above-ascribed meanings, has two functions: it serves as a reactant and its stoichiometric excess serves as solvent or suspending medium in which the reaction proceeds.

The reaction is preferably carried out while cooling or at an elevated temperature, preferably at temperatures between 0° C and 120° C, in particular between 25° and 75° C, or at the boiling temperature of the solvent or of the suspension.

Usually, the Friedel-Crafts-type catalyst is added to the reaction mixture at room temperature. Thereby, the temperature of the mixture increases as the reaction proceeds. The condensation is completed by continuing heating the mixture, for example on a water bath, for a short period of time. The reaction product, which is a complex of the catalyst and the final product of formula I, Ia or I*, is readily decomposed by pouring the reaction mixture into a mixture of ice water and concentrated acid, e.g. hydrochloric acid or sulfuric acid. On addition of the acid the compounds of formula This reaction is illustrated by the following equation:

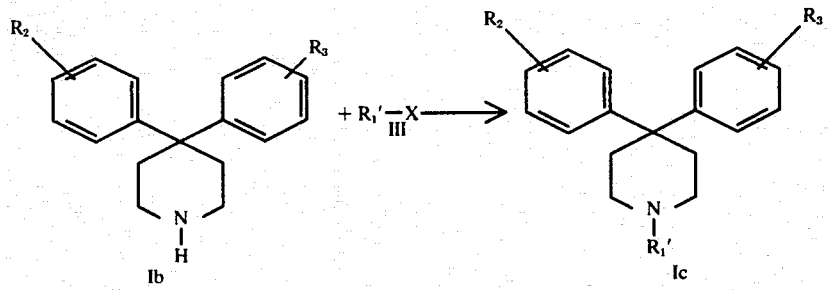

I, Ia or I* can be isolated in the form of their acid-addition salts, which are readily crystallized from polar solvents, e.g. acetic acid alkyl esters, lower alkanols, ethers or ketones. The acid-addition salt is converted into the corresponding free base of formula I, Ia or I* by rendering alkaline an aqueous acid solution containing I, Ia or I* by the addition thereto of an aqueous alkaline solution, whereby the mixture is cooled. The alkalized mixture can be extracted with ether. The ether extracts contain the 4,4-diarylpiperidine base and are dried over known drying agents or desiccants. By evaporation of the ether the crude base is obtained as a residue which is purified by distillation or by recrystallization, e.g., from aqueous dimethylformamide, lower alkanols or ketones.

The acid-solution salts of the 4,4-diphenylpiperidine compounds of formula I are produced by methods known to the art, for instance, by dissolving the base in a suitable solvent wherein the respective salt is insoluble and adding thereto the corresponding acid which may also be dissolved in a suitable solvent. The hydrochloride can be obtained directly by decomposing the reaction product, obtained by proceeding as described hereinabove, with ice water-hydrochloric acid. Of course, not only acid-addition salts with inorganic salts, such as the hydrochlorides, hydrobromides, sulfates, nitrates, phosphates, and others, can be produced but also acid-addition salts with organic acids, such as the salts with acetic acid, propionic acid, and other alkanoic acids, maleic acids, fumaric acid, lactic acid, citric acid, malic acid, tartaric acid, succinic acid, glycine, alanine and other amino acids, benzoic acid, salicyclic acid, phthalic acid, furoic acid, nicotinic acid, isonicotinic acid, and others. The preferred acid addition salts are, of course, those salts which are substantially non-toxic and pharmaceutically acceptable in amounts administered.

To produce the compounds of the formulae I, Ia or I* wherein $R_1$ is other than hydrogen, a 4,4-diphenyl-piperidine of formula Ib is produced (see formula Ib below) by the process described hereinabove or by any other process. Then a compound of formula III $R_1'-X$         III wherein
$R_1'$ has one of the above-ascribed meanings of $R_1$, except that $R_1'$ is not a hydrogen atom (—H), while
X is a reactive functional group, preferably halogen, in particular a halogen atom having an atomic number from 17 to 53, e.g. bromine, chlorine and iodine.

Thus compounds of formula Ic, in which R', $R_2$ and $R_3$ indicate the substituents mentioned above, are obtained. This process is of special advantage when producing compounds of formula Ic wherein $R_1'$ is alkyl, which compounds can be considered as the pharmacologically most effective ones. As X is eliminated during the reaction Ib → Ic, its identity within the limits specified is of little practical importance.

B. 4,4-DIARYLPIPERIDINE COMPOUNDS 4,4-Diphenylpiperidine compounds of the following formula Id have been produced for the first time according to the present invention:

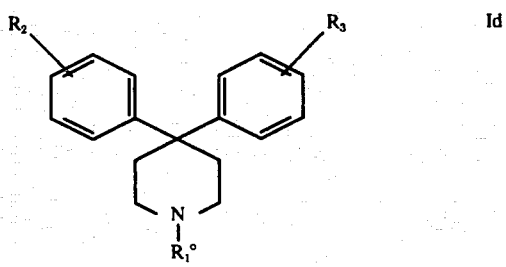

In said formula Id
$R_2$ and $R_3$ indicate the same substituents as mentioned hereinabove, while
$R_1°$ indicates a hydrogen atom (—H), straight chain alkyl with 2 to 6 carbon atoms, isopropyl, tertiary butyl, branched chain alkyl with 5 and 6 carbon atoms, nuclearly-substituted or unsubstituted phen(lower)alkyl, hydroxy(lower)alkyl, (lower)alkyl[carbonyl or oxo](lower)alkyl, (lower)alkoxy(lower)alkyl, nuclearly-substituted or unsubstituted phenoxy(lower)alkyl, nuclearly-substituted or unsubstituted phenyl[carbonyl or oxo](lower)alkyl, nuclearly-substituted or unsubstituted phen(lower)alkoxy(lower)alkyl; wherein each occurrence of the designation "lower" denotes the respective carbon skeleton having 1 to 4 carbon atoms; any substituent of nuclearly substituted phen(lower)alkyl, phenoxy(lower)alkyl, phen(lower)alkoxy(lower)alkyl or phenyl[carbonyl or oxo](lower)alkyl being a halogen atom having an atomic number from 9 to 35, in particular fluorine or chlorine.

The preferred novel compounds of the present invention have the following formula

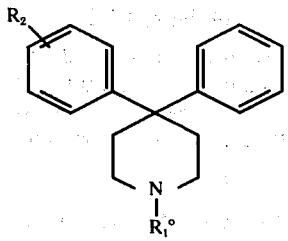

wherein $R_1°$ and $R_2$ have their above-ascribed meanings. The most preferred novel compounds of the present invention are 1-ethyl-4,4-diphenylpiperidine,
1-isopropyl-4,4-diphenylpiperidine,
1-tertiary-butyl-4,4-diphenylpiperidine,
1-n-butyl-4,4-diphenylpiperidine,
1-n-amyl-4,4-diphenylpiperidine,
1-isoamyl-4,4-diphenylpiperidine,
1-n-hexyl-4,4-diphenylpiperidine,
1-isopropyl-4-phenyl-4-(p-tolyl)piperidine,
1-(benzyl)-4,4-diphenylpiperidine,
1-(2-phenylethyl)-4,4-diphenylpiperidine,
1-(1-phenyl-2-propyl)-4,4-diphenylpiperidine,
1-(3-methoxypropyl)-4,4-diphenylpiperidine,
1-(2-hydroxyethyl)-4,4-diphenylpiperidine,
1-(3-hydroxypropyl)-4,4-diphenylpiperidine,
1-(2-methoxyethyl)-4,4-diphenylpiperidine,
1-acetonyl-4,4-diphenylpiperidine,
1-(2-phenoxyethyl)-4,4-diphenylpiperidine,
1-(3-phenoxy-2-hydroxypropyl)-4,4-diphenylpiperidine,
1-(2-phenyl-2-oxoethyl)-4,4-diphenylpiperidine,
4,4-diphenylpiperidine,
1-(p-chlorobenzyl)-4,4-diphenylpiperidine,
1-(3-p-fluorobenzoyl)propyl-4,4-diphenylpiperidine,
1-(3-benzoylpropyl)-4,4-diphenylpiperidine and others, as well as their pharmacologically-acceptable acid addition salts.

The present invention further encompasses acid addition salts or salts of the novel compounds with an organic or inorganic acid. Examples for inorganic acids are hydrochloric acid, hydrobromic acid and sulfuric acid. An example for an organic acid is tataric acid. The acid used can be a monobasic acid, such as an alkanesulfonic acid, e.g. methanesulfonic acid ($H_3C—SO_3H$), acetic acid, lactic acid, camphor sulfonic acid, p-chlorobenzene sulfonic acid, cyclopentanepropionic acid, heptanoic acid, 2-(p-hydroxybenzoyl)benzoic acid, 2-naphthalene sulfonic acid, p-toluenesulfonic acid or trimethylacetic acid. The acid used may be a dibasic acid, e.g. succinic acid, adipic acid, 1,2-ethanedisulfonic acid, 4,4-methylenebi-(3-hydroxy-2-naphthoic acid); a tribasic acid, e.g. phosphoric acid and citric acid; a saturated acid, e.g. propionic acid; an ethylenically-unsaturated acid, e.g. maleic acid and fumaric acid; and an aromatic acid, such as salicyclic acid. Preferred acid-addition salts are those which are physiologically active and pharmaceutically-acceptable.

C. UTILITY OF 4,4-DIPHENYLPIPERIDINES, PHARMACEUTICAL COMPOSITIONS CONTAINING SAME AND APPLICATION IN MEDICINE

In view of the fact that prior art (in pharmacological tests) has reported 4,4-diphenylpiperidines to be devoid of useful physiological activity [1 methyl-4,4-diphenylpiperidine was reported to be devoid of analgesic action and the same compound together with 1-(secondary butyl)-4,4-diphenylpiperidine was reported to be devoid of any therapeutically-utilizable antihistaminic activity], it was entirely unexpected that these and structurally related 4,4-diphenylpiperidine compounds possess valuable and unforeseen pharmacological properties. Whereas other piperidine derivatives may possess analgesic, sedative or antihistaminic properties, all compounds of formulae I, I*, Ia, Ib, Ic, Id and Ie [other than those wherein $R_1$ is nuclearly-substituted or unsubstituted phenyloxo(lower)alkyl] and their acid addition salts are distinguished by their central nervous system stimulating activity, especially on oral and parenteral administration. This entirely unexpected effect sets in on administration of a low dose and lasts for a prolonged period of time.

Said stimulating effect manifests itself by increased attentiveness, alertness, and vigilance without causing locomotory activity accompanied by restlessness and without inducing aggressiveness. The central nervous ystem (CNS) stimulating 4,4-diphenylpiperidines of formulae I, I*, Ia through Ie and their therapeutically-acceptable acid addition salts thus possess considerable advantages over the heretofore known and used central nervous system stimulating agents of the amphetamine type. In contrast to said amphetamine-type compounds the compounds of formula I, I*, Ia through Ie do not cause a pronounced increase in blood pressure nor general stimulation of the sympathetic nervous system. Due to these pharmacological properties the compounds have proved of value in therapy for all indications in which stimulation of the central nervous system is required, such as in the treatment of chronic fatigue, depressions especially in certain psychotic, senile, and psychoneurotic patients, obesity, and others. Therefore the compounds of formulae I, I*, Ia through Ie and their pharmacologically-compatible salts with organic or inorganic acids are useful as medicaments; furthermore the compounds of formula Ib are valuable intermediates for the preparation of compounds of formulae Ic, Id and Ie.

A further object of this invention is a method of treating neurological disorders of the motoric system cuased by a disturbed regulation of the motoric transmission of an individual with a therapeutically effective amount of a compound of formula I, I* and Ia through Ie. By administration of the disclosed compounds to the afflicted individual an improvement of the regulation of the motoric transmission of the diseased subject is achieved and neurological disorders, such as parkinsonism, parkinsonoid, tremor of other genesis, e.g. tremor caused by intoxication or overdosage of neuroleptics, could be softened. A further object of this invention is a method of treating depressive syndroms of a subject afflicted with such syndroms with a therapeutically effective amount of the new compound stimulating the central nervous system. This treatment according to the invention causes mood elevation in cases of retarded depressions.

A further object of this invention is a method of support to the withdrawal of addicting drugs. More particularly, this method counteracts and diminishes the appearance of withdrawal symptoms.

It has been found, that the CNS stimulating compounds of the invention, while exhibiting similar stimulation of the central nervous system as the addicting drugs, do not cause habituation, tolerance and hence do not lead to drug-addiction. On repeated daily chronic administration of the same dose of the new substances to mice, rats and dogs, the same degree of stimulation has been reproduced. The animals tested did not develop habituation or tolerance as a consequence of repeated administration. Disruption of a continuous treatment over more than ten days did not provoke the appearance of withdrawal symptoms.

Medicaments or pharmaceutical compositions which contain one or more compounds of formula I (in a free form or in the form of a pharamacologically-compatible acid addition salt) as active substance can, but need not, contain other pharmacologically-active substances.

As stated above, the 4,4-diphenylpiperidine compounds are preferably administered orally. Compositions for oral administration comprise, for instance, tablets, pills, dragees, lozenges, and the like shaped preparations.

The compounds may also be administered in powder or granulated form, preferably enclosed in gelatin and the like capsules. Oral administrated in liquid form, such as in the form of emulsions, suspensions, sirups, and the like, is also possible. These solid and liquid preparations are produced in a manner known to the art of compounding and processing pharmaceutical compositions. The novel compositions are suitably presented in unit dosage form, whereby each unit contains a predetermined amount of the 4,4-diphenylpiperidine compound as required to produce the desired therapeutic effect.

For preparing the solid compositions, a 4,4-diphenylpiperidine compound is mixed with conventional carriers and excipients, such as diluting agents, binding agents, lubricants, expanding agents, for instance, with glucose, lactose, mannitol, corn starch, potato starch, dextrin, talc, kaolin, magnesium hydroxide, magnesium carbonate, bentonite, magnesium trisilicate, pectin, gelatin, agar, stearic acid, magnesium stearate, calcium stearate, gums, and others.

Tablets, pills, or other shaped compositions in, e.g., unit dosage form may be provided with an enteric coating which resists disintegration in the stomach but releases the active agent in the intestines. A number of materials are used for such enteric coatings, such as shellac, cellulose acetate phthalate and others.

The pharmaceutical preparations contain from approximately 0.1 to 75%, preferably from 1 to approximately 50%, by weight of the active substance.

Individual doses of active substance are between 0.07 and 1, preferably from 0.14 to 1, mg/kg of body weight. For application in human medicine these doses correspond to an individual dose of approximately 5 to 70, preferably 10 to 50, mg of active substance.

The indicated doses are administered 1 to 4 times daily, preferably in 2 equal doses daily. While oral administration in the form of pills, tablets, dragees, capsules, and the like preparations is preferred, parenteral or rectal administration may also be employed.

DESCRIPTION OF THE PREFERRED EMBODIMENTS

The following examples serve to illustrate the production of the compounds of formulae I, I* and Ia through Ie, according to the novel process of the present invention without, however, being limited thereto.

EXAMPLE 1

1-Methyl-4,4-diphenylpiperdine 20 g. of 1-methyl-4-hydroxy-4-phenylpiperidine are suspended in 150 ml. of anhydrous benzene. 61.5 g. of finely pulverized anhydrous aluminum chloride are added in portions thereto within 25 minutes while stirring. The reaction temperature increases on starting addition of aluminum chloride to about 45° C. After about 20 minutes the temperature is increased to and maintained at about 50° to 55° C. for about 1 hour. The resulting reaction solution is cooled to about 20° C. and is poured into a mixture of ice and concentrated hydrochloric acid. After warming the mixture to room temperature, the hydrochloric acid layer together with the dark oil formed on decomposition is separated from the benzene layer and is washed with benzene. Water is added to said hydrochloric acid-oil phase, while stirring, in portions and in an amount sufficient to produce an almost clear solution. Said acid solution is rendered alkaline by the addition of 40 % sodium hydroxide solution whereby the mixture is well cooled. The alkalized mixture is repeatedly extracted with ether. The combined ether extracts are dried over anhydrous potassium carbonate and are concentrated by evaporation of the ether. 24 g. of the crude base are obtained as residue in the form of yellowish oil. A water clear oil boiling at 98° to 103° C./0.01 mm. Hg is recovered by distillation of said crude oil in a high vacuum. The oil solidifies to crystals on standing for a short period of time. After recrystallization from aqueous dimethylformamide, the resulting 1-methyl-4,4-diphenylpiperidine has a melting point of 71° to 73° C.

Its hydrochloride is produced by dissolving the base in acetic acid ethyl ester and adding an ethereal hydrochloric acid solution thereto. After recrystallization from acetic acid ethyl ester, the melting point of the hydrochloride is 220° to 223° C.

EXAMPLE 2

1-Methyl-4,4-diphenylpiperidine 100 g. of 1-methyl-3-benzoyl-4-hydroxy-4-phenylpiperidine are suspended in 600 ml. of anhydrous benzene while stirring. 200 g. of finely pulverized, anhydrous aluminum chloride are added in portions thereto within 25 minutes. The reaction temperature increases to about 45° C. when adding the first portion of aluminum chloride. After about 20 minutes the reaction temperature of the reaction mixture is maintained at 50° to 55° C. for about 1 hour. The reaction mixture is then cooled to room temperature and is introduced into a mixture of ice and concentrated hydrochloric acid while stirring. After heating the mixture to room temperature, the benzene layer is separated from the hydrochloric acid and oil layer which is washed with benzene. The hydrochloric acid and oil layer is diluted, while stirring, with an amount of water sufficient to cause substantially all the oil to be dissolved. The resulting aqueous solution is then rendered alkaline by the addition of 40% sodium hydroxide solution, while stirring, and the alkaline solution is extracted with ether. The combined ether extracts are dried over anhydrous potassium carbonate and are concentrated by evaporation of the ether. 83.5 g. of the crude base are obtained as residue in the form of a dark oil. A light oil boiling at 98° to 103° C./0.01 mm. Hg is recovered by distillation of said crude oil in a high vacuum. The oil solidifies to crystals on standing for a short period of time. After recrystallization from aqueous dimethylformamide, the resulting 1-methyl-4,4-diphenylpiperidine has a melting point of 71° to 73° C.

EXAMPLE 3

1-Ethyl-4,4-diphenylpiperidine

When proceeding as described in Example 2 but replacing the corresponding 1-methyl-3-benzoyl-4-hydroxy-4-phenylpiperidine starting material by 1-ethyl-3-benzoyl-4-hydroxy-4-phenylpiperidine and reacting 20 g. thereof with benzene in the presence of aluminum chloride, 15 g. of crude 1-ethyl-4,4-diphenylpiperidine base boiling at 110° to 123° C./0.01 mm. Hg are obtained. Its acid addition salt with maleic acid is produced by the addition of maleic acid to its acetone solution. The maleic acid salt melts at 239° to 240° C.

EXAMPLE 4

1-Isopropyl-4,4-diphenylpiperidine

When proceeding as described in Example 2 but replacing the corresponding 1-methyl-3-benzoyl-4-hydroxy-4-phenylpiperidine by 1-isopropyl-3-benzoyl-4-hydroxy-4-phenylpiperidine and reacting 55 g. thereof with benzene in the presence of anhydrous aluminum chloride, 33 g. of crude 1-isopropyl-4,4-diphenylpiperidine base boiling at 117° to 125° C./0.01 mm. Hg are obtained in the form of a yellowish viscous oil. On adding isopropanol saturated with hydrogen chloride to its acetic acid ethyl ester solution, the crystalline hydrochloride precipitates. After recrystallization from isopropanol, the hydrochloride melts at 267° C.

EXAMPLE 5

1-Phenethyl-4,4-diphenylpiperidine

When proceeding as described in Example 2 but replacing the corresponding 1-methyl-3-benzoyl-4-hydroxy-4-phenylpiperidine by 1-phenethyl-3-benzoyl-4-hydroxy-4-phenylpiperidine and reacting 20 g. thereof with benzene in the presence of anhydrous aluminum chloride, 15 g. of 1-phenethyl-4,4-diphenylpiperidine base are obtained. On adding ether saturated with hydrogen chloride to its acetic acid ethyl ester solution, the crystalline hydrochloride precipitates. After recrystallization from isopropanol, the hydrochloride melts at 202° to 204° C.

EXAMPLE 6

1-Isopropyl-4-phenyl-4-(p-tolyl)piperidine

When proceeding as described in Example 2 but replacing the corresponding 1-methyl-3-benzoyl-4-hydroxy-4-phenylpiperidine by 1-isopropyl-3-(p-toluoyl)-4-hydroxy-4-(p-tolyl)piperidine and reacting 20 g. thereof with benzene in the presence of 30 g. of aluminu chloride, 17 g. of the hydrochloride of 1-isopropyl-4-phenyl-4-(p-tolyl)piperidine are isolated on decomposing the reaction mixture with a mixture of ice and hydrochloric acid. After recrystallization from isopropanol, the hydrochloride is obtained in colorless leaflets of the melting point 271° to 273° C.

EXAMPLE 7

1-(3-Methoxypropyl)-4,4-diphenylpiperidine 30 g. of 1-(3-methoxypropyl)-3-benzoyl-4-hydroxy-4-phenylpiperidine are suspended in 225 ml. of anhydrous benzene. 50 g. of finely pulverized, anhydrous aluminum chloride are added thereto within 20 minutes, while stirring. The reaction temperature increases during said addition up to 60° C. The reaction mixture is then kept at from 50° to 55° C. for about 1 hour, is cooled to room temperature, and is added to a mixture of ice and concentrated hydrochloric acid. The benzene layer is separated from the aqueous layer by means of a separating funnel and is washed once with dilute hydrochloric acid. The combined aqueous layers are rendered alkaline by the addition of 40% sodium hydroxide solution. The precipitated base is separated by repeated extraction with ether. The combined ether extracts are dried over anhydrous potassium carbonate and the ether is distilled off. 21 g. of the crude base remain as residue. On distillation in a high vacuum, pure 1-(3-methoxypropyl)-4,4-diphenylpiperidine is obtained in the form of a light oil boiling at 130° C./0.01 mm. Hg.

The crystalline fumaric acid salt of said base is obtained by the addition of the calculated amount of fumaric acid to the solution of the base in isopropanol. After recrystallization from isopropanol, the fumaric acid salt melts at 189° to 190° C.

EXAMPLE 8

1-(1-Phenyl-2-propyl)-4,4-diphenylpiperidine

When proceeding as described in Example 2 but replacing the corresponding 1-methyl-3-benzoyl-4-hydroxy-4-phenylpiperidine by 1-(1-phenyl-2-propyl)-3-benzoyl-4-hydroxy-4-phenylpiperidine and reacting 20 g. thereof with benzene in the presence of anhydrous aluminum chloride, 1-(1-phenyl-2-propyl)-4,4-diphenylpiperidine hydrochloride is isolated on decomposing the reaction mixture with a mixture of ice and concentrated hydrochloric acid. The yield of the crude hydrochloride amounts to 15 g. After recrystallization from isopropanol, its melting pont is 172° to 174° C.

EXAMPLE 9

1-(2-Hydroxyethyl)-4,4-diphenylpiperidine

When proceeding as described in Example 2 but replacing the corresponding 1-methyl-3-benzoyl-4-hydroxy-4-phenylpiperidine by 1-(2-hydroxyethyl)-3-benzoyl-4-hydroxy-4-phenylpiperidine and reacting 20 g thereof with benzene in the presence of anhydrous aluminum chloride, 10 g. of 1-(2-hydroxyethyl)-4,4-diphenyl-piperidine base boiling at from 160° to 167° C/0.01 mm. Hg are obtained. The hydrochloride obtained from the isopropanol solution of said base has a melting point of 219° to 221° C.

EXAMPLE 10

1-Benzyl-4,4-diphenylpiperidine

When proceeding as described in Example 2 but replacing the corresponding 1-methyl-3-benzoyl-4-hydroxy-4-phenylpiperidine by 1-benzyl-3-benzoyl-4-hydroxy-4-phenylpiperidine and reacting 20 g. thereof with benzene in the presence of anhydrous aluminum chloride and decomposing the reaction product with a mixture of ice and hydrochloric acid, 14 g. of the hydrochloride of 1-benzyl-4,4-diphenylpiperidine are isolated in crystalline form. After recrystallization from isopropanol, the hydrochloride melts at 239° C.

EXAMPLE 11

1-(2-Phenoxyethyl)-4,4-diphenylpiperidine

When proceeding as described in Example 2 but replacing the corresponding 1-methyl-3-benzoyl-4-hydroxy-4-phenylpiperidine by 1-(2-phenoxyethyl)-3-benzoyl-4-hydroxy-4-phenylpiperidine and reacting 20 g. thereof with benzene in the presence of anhydrous aluminum chloride, 13 g. of 1-(2-phenoxyethyl)-4,4-diphenylpiperidine are obtained. Its boiling point is 145° C./0.01 mm. Hg. The compound yields a fumaric acid salt melting at 199.5° C.

When proceeding as described in the preceding examples but using other starting materials than those given therein and reacting said starting materials with benzene in the presence of aluminum chloride, the following compounds are produced:

| Ex. No. | Starting reactant | Condensation product | Process of Examples |
|---|---|---|---|
| 12 | 1-(n-Butyl)-3-benzoyl-4-hydroxy-4-phenylpiperidine | 1-(n-Butyl)-4,4-diphenylpiperidine | 2 |
| 13 | 1-(Isoamyl)-3-benzoyl-4-hydroxy-4-phenylpiperidine | 1-(Isoamyl)-4,4-diphenylpiperidine | 2 |
| 14 | 1-(n-Hexyl)-4-hydroxy-4-phenylpiperidine | 1-(n-Hexyl)-4,4-diphenylpiperidine | 1 |
| 15 | 1-(tertiary Butyl)-4-hydroxy-4-phenylpiperidine | 1-(teriary Butyl)-4,4-diphenylpiperidine | 1 |
| 16 | 1-Benzyl-4-hydroxy-4-(p-tolyl)piperidine | 1-Benzyl-4-(p-tolyl)-4-phenylpiperidine | 1 |
| 17 | 1-Acetonyl-4-hydroxy-4-phenylpiperidine | 1-Acetonyl-4,4-diphenylpiperidine | 1 |
| 18 | 1-Phenylcarbonylmethyl-4-hydroxy-4-phenylpiperidine | 1-Phenylcarbonylmethyl-4,4-diphenylpiperidine | 1 |
| 19 | 4-Phenyl-4-hydroxypiperidine | 4,4-Diphenylpiperidine | 1 |
| 20 | 4-(p-Tolyl)-4-hydroxypiperidine | 4-Phenyl-4-(p-tolyl)piperidine | 1 |

Of course, other compounds of formula I are also produced as described hereinabove.

The following examples serve to illustrate pharmaceutical compositions containing the 4,4-diphenylpiperidine compounds without, however, being limited thereto.

EXAMPLE 21

Tablets

Composition:
20 g. of 1-isopropyl-4,4-diphenylpiperidine hydrochloride,
250 g. of corn starch,
485 g. of lactose,
200 g. of talc,
25 g. of magnesium stearate, and
15 g. of gelatin.

The 1-isopropyl-4,4-diphenylpiperidine is intimately mixed with the corn starch and lactose, granulated with a 10% gelatin solution in water, passed through a No. 8 screen, and dried. The dried granules are thoroughly mixed with the talc and the magnesium stearate and compressed into tablets, each weighing about 200 mg. and containing 10 mg. of 1-isopropyl-4,4-diphenylpiperidine hydrochloride.

EXAMPLE 22

The 1-isopropyl-4,4-diphenylpiperidine hydrochloride of Example 21 is replaced by equal amounts of other 4,4-diphenylpiperidine compounds, such as
1-ethyl-4,4-diphenylpiperidine maleinate,
1-methyl-4,4-diphenylpiperidine hydrochloride,
1-isopropyl-4-phenyl-4-(p-tolyl)piperidine hydrochloride.
1-(phenethyl)-4,4-diphenylpiperidine hydrochloride,
1-(3-methoxypropyl)-4,4-diphenylpiperidine fumarate,
1-(1-phenyl-2-propyl)-4,4-diphenylpiperidine hydrochloride,
1-(2-hydroxyethyl)-4,4-diphenylpiperidine hydrochloride,
1-benzyl-4,4-diphenylpiperidine hydrochloride,
1-(2-phenoxyethyl)-4,4-diphenylpiperidine fumarate,
and other 4,4-diphenylpiperidine compounds of formula I. Otherwise the procedure is the same as described in Example 21 and the resulting tablets contain about 10 mg. of the active agent per tablet.

EXAMPLE 23

Sugar coated dragees

The tablets obtained according to Examples 21 and 22 are used as cores for making dragees. They are coated by rotating in a coating pan with a sugar solution. Sugar coating is repeated until each dragee has attained a weight of about 300 mg.

EXAMPLE 24

Gelatin capsules 50 g. of crystalline 1-methyl-4,4-diphenylpiperidine base are intimately mixed with 1500 g. of corn starch and 50 g. of magnesium stearate. The mixture is filled into two-piece hard gelatin capsules. Each capsule contains 160 mg. of the mixture and 5 mg. of the active 1-methyl-4,4-diphenylpiperidine. The capsules are given in the treatment of depressive conditions in a dose of 3 to 5 capsules daily.

Other orally administrable compositions are prepared according to methods well known to the art. Liquid compositions are, likewise, produced by incorporating the active 4,4-diphenylpiperidine compounds into aqueous solutions, suspensions, emulsions, and similar liqud pharmaceutical vehicles whereby, if requred, suitable dispersing or suspending agents, such as synthetic and natural gums, for instance, tragacanth, alginates, methyl cellulose, polyvinyl pyrrolidone, dextran, and others are used for dispersing the active agent.

Rectal administration by means of suppositories is further alternative. such suppositories are prepared by incorporating the active 4,4-diphenylpiperidine compound into a molten conventional suppository base, for instance, into cocoa butter, polyoxyethylene waxes, and others.

The following 4,4-diphenylpiperidine compounds have been produced in addition to those described hereinabove in Examples 1 to 20.

EXAMPLE 25

1-(p-Chlorobenzyl)-4,4-diphenylpiperidine

When proceeding as described in Example 2, but replacing 1-methyl-3-benzoyl-4-hydroxy-4-phenyl-piperidine (used as starting material in said example) by 1-(p-chlorobenzyl)-3-benzoyl-4-hydroxy-4-phenyl-piperidine, 1-(p-chlorobenzyl)-4,4-diphenylpiperidine is obtained. It precipitates from the acid layer directly in the form of its crystalline hydrochloride. After recrystallization from isopropanol, the hydrochloride melts at 249° to 251° C.

EXAMPLE 26

1-(secondary Butyl)-4,4-diphenylpiperidine

When proceeding as described in Example 2, but replacing 1-methyl-3-benzoyl-4-hydroxy-4-phenyl-piperidine (used as starting material in said example) by 1-secondary butyl-3-benzoyl-4-phenyl-4-hydroxypiperidine and reacting 25 g. thereof with benzene in the presence of aluminum chloride, 17 g. of the crude base 1-secondary butyl-4,4-diphenylpiperidine are obtained. The crude base is not purified by distillation in a high vacuum but by adding ether saturated with hydrogen chloride to its solution in acetic acid ethyl ester. Thereby, the crystalline hydrochloride is precipitated. It melts at 242° to 245° C. (with decomposition) after recrystallization from acetic acid ethyl ester.

EXAMPLE 27

4,4-Diphenylpiperidine

A phenyl lithium solution is prepared by reacting 50.5 g. of bromobenzene and 4.3 g. of metallic lithium in 400 cc. of ether. 41.7 g. of 1-benzylpiperidone-(4) are added thereto at 0° C. in a nitrogen atmosphere within 30 minutes while stirring. The reaction is completed by keeping the reaction mixture at room temperature for 3 more hours. The reaction mixture is cooled to 0° C. and is decomposed by slowly adding 250 cc. of water thereto.

The separated aqueous layer is removed and the ether layer is dried over sodium sulfate. 65 g. of 1-benzyl-4-phenyl-4-hydroxypiperidine remain after distilling off the ether, and are recrystallized from benzene. The pure base has a melting point of 102° to 103° C.

50 g. of the pure base in 1000 cc. of ethanol to which 50 cc. of water have been added, are hydrogenated at 80° C. with hydrogen in an autoclave at a pressure of 10 atmospheres gauge in the presence of 10 g. of a catalyst containing 5% of metallic palladium precipitated on barium sulfate, within about 7 hours. After cooling, the catalyst is filtered off and the solvent is distilled off completely. 34 g. of 4-phenyl-4-hydroxy-piperidine remain as residue. After recrystallization from acetone, the pure compound has a melting point of 154° to 156° C.

When proceeding as described in Example 1, but replacing 1-methyl-4-hydroxy-4-phenylpiperidine (used as starting material in said example) by 4-phenyl-4-hydroxypiperidine and reacting 17.8 g. thereof with benzene in the presence of aluminum chloride, 12.0 g. of 4,4-diphenylpiperidine hydrochloride are obtained. Said hydrochloride melts at 300° C. (with decomposition) after recrystallization from a mixture of ethanol and isopropanol. The 4,4-diphenylpiperidine base melts at 70° to 72° C.

EXAMPLE 28

1-[3-(p-Fluorobenzoyl)propyl]-4,4-diphenylpiperidine 6.1 g. of 4,4-diphenylpiperidine are heated to boiling with 6.2 g. of 3-(p-fluorobenzoyl)propyl iodide and 5.3 g of anhydrous sodium carbonate in 30 cc. of methyl ethyl ketone for 8 hours while stirring. After cooling, the precipitated salt is filtered off and the filtrate is evaporated to dryness. The residue is dissolved in water and the aqueous solution is rendered alkaline by the addition of sodium hydroxide solution. The resulting base is recovered by repeated extraction with ether. The combined ether extracts are dried over potassium carbonate, the ether is distilled off, and the residue is recrystallized from ethanol with the addition of activated charcoal. Thereby, 9 g. of 1-[3-(p-fluorobenzoyl)propyl]-4,4-diphenylpiperidine of the melting point 107° to 108° C. are obtained. On adding fumaric acid to its solution in ether, the furmarate of the melting point 195° to 197° C. is obtained.

EXAMPLE 29

1-(3-Benzoylpropyl)-4,4-diphenylpiperidine

When proceeding as described in Example 28, but replacing 3-(p-fluorobenzoyl)propyl iodide (used as the one reactant in said example) by 3-benzoylpropyl iodide and reacting 27.4 g. of said 3-benzoylpropyl iodide with 24.4 g. of 4,4-diphenylpiperidine, on addition of hydrochoric acid to the etheric solution of the diphenylpiperidine base 19.5 g. of 1-(3-benzoylpropl)-4,4-diphenylpiperidine hydrochloride are obtained. On recrystallization from ethanol, the hydrochloride melts at 200° C.

EXAMPLE 30

1-(3-Hydroxypropl)-4,4-diphenylpiperidine

When proceeding as described in Example 2, but replacing 1-methyl-3-benzoyl-4-hydroxy-4-phenyl-piperidine (used as starting material in said example) by 1-(3-hydroxypropyl)-3-benzoyl-4-hydroxy-4-phenylpiperidine and reacting 80 g. thereof with benzene in the presence of aluminum chloride, 50 g. of 1-(3-hydroxypropyl)-4,4-diphenylpiperidine are obtained. The boiling point of said crude base is from 173° to 182° C./0.01 mm. Hg. Its hydrochloride has a melting point of 233° to 234.5° C.

It is evident from these examples that the phenyl ring in compounds wherein $R_1$ is phen(lower)alkyl, phenoxy-(lower)alkyl, phenoxo(lower)alkyl, or phen(-lower)alkoxy-(lower)alkyl can be mono-substituted, for instance, by halogen, preferably by chlorine or fluorine. Such substituents $R_1$ are, for instance, chloro-benzyl, fluorobenzoyl-propyl and others. The above described novel compounds with substituents in the phenyl ring also have a pronounced central nervous system stimulating activity on oral administration and thus are useful as effective agents for treating humans and animals for disorders requiring such stimulation.

EXAMPLE 31

1-Methyl-4,4-diphenylpiperidine 10 g. of 1-methyl-4-hydroxy-4-phenylpiperidine are dissolved in 340 ml. of anhydrous benzene. The solution is addeded at from 60° C in portions to a suspension of 37 g. of anhydrous iron trichloride in 100 ml. anhydrous benzene within 60 minutes while stirring.

The reaction mixture is kept stirring at from about 70° to 75° C for about 5 hours. The batch is cooled to room temperature and is poured into a mixture of ice and concentrated hydrochloric acid and ether. The acid aqueous phase is diluted with water to produce an almost clear solution, separated from the ether layer, washed with ether and rendered alkaline by the addition of 40% sodium hydroxide solution while cooling. The piperidine base separates and is taken up with ether and the alkalized mixture repeatedly extracted with ether. The combined ether solutions are dried over anhydrous pottasium carbonate and the ether evaporated. 11 g. of the crude base are obtained, which on distillation at 98° to 100° C./0.01 mm./Hg yields 8.8 g. of 1-methyl-4,4-diphenylpiperidine, which has a melting point of 71° to 72° C after recrystallization.

EXAMPLE 32

1-(2-Acetoethyl)-4,4-diphenylpiperidine

When proceeding as described in Example 2, but replacing 1-methyl-3-benzoyl-4-hydroxy-4-phenyl-piperidine (as starting material in said example) by 1-(2-acetoethyl)-3-benzoyl-4-hydroxy-4-phenylpiperidine and reacting 70 g. thereof with benzene in the presence of aluminum chloride, 40 g. of 1-(2-acetoethyl)-4,4-diphenylpiperidine are obtained.

PHARMACOLOGICAL TESTS

As stated above, the compounds of formula I have advantageous central nervous system stimulating properties. Side-effects, as they are encountered on administration of amphetamine-type stimulants, are produced to a much lesser extent by the 4,4-diphenylpiperidine compounds, if at all. The following Table 1 demonstrates, for instance, the advantages of 1-isopropyl-4,4-diphenylpiperidine over amphetamine. The tests were carried out according to known and accepted pharmacological standard test methods.

TABLE 1

| No. | Test | 1-Isopropyl-4,4-diphenylpiperidine | Amphetamine |
|---|---|---|---|
| a | Acute toxicity albino mouse perorally | 150 mg./kg. | 100 mg./kg. |
| b | Locomotory activity (restlessness in movements); albino mouse 5 mg/kg. perorally | Increase by 20 % | Increase by 100 % |
| c | Saliva secretion albino mouse | No secretion | Pronounced |
| d | Increase in blood pressure (rats and dogs) | Slight increase | Pronounced increase |
| e | Potentiating effect on noradrenaline | Present | Present |
| f | Exophthalmus | Absent | Present |
| g | Tachyphylaxis | None | Pronounced |

The compounds of the other examples show also the above advantages over amphetamine-type stimulants.

The central nervous system stimulating effect of the 4,4-diarylpiperidine compounds of formula I was determined by known and accepted pharmacological standard test methods and was found to be about equal, and with respect to some compounds even superior, to that of amphetamine-type stimulants.

The following Table 2 demonstrates the new pharmacological effects of the compounds of the subject invention Specifically in pharmacological standard tests, the compounds of Examples 1, 3 to 5, 7, 9, 10, 17, 19, 26, 30 and 32 produce, administered to the albino mouse, a strong increase of the vigilance of the animal, whereas the locomotory activity is only slightly increased without causing restlessness, sterotypia or salivation. All these drugs show a pronounced anticataleptic action and nearly all drugs exhibit strong tremonin antagonism.

The compounds of formula I wherein $R_1$ is nuclearly-substituted or unsubstituted phenyloxo(lower)alkyl, e.g. those of Example 28 and 29, exhibit anticataleptic action, but furthermore show a very low acute toxicity. These compounds somewhat reduce vigilance and induce sedation of animals they potentiate the effect of hexobarbital and exhibit neuroleptic effects. These compounds are useful as neuroleptics.

TABLE 2

| Compound of Example | Acute toxicity in the albino mouse $LD_{50}$ (mg/kg) i.v. | (mg/kg) p.o. | General behaviour of the albino mouse with different doses* | | | |
|---|---|---|---|---|---|---|
| | | | Vigilance | Locomotory activity | Restlessness Stereotype | Salivation |
| 19 | 25 | | ++ | (+) | φ | φ |
| 1 | 45 | 140 | ++ | (+) | φ | φ |
| 10 | 20 | | ++ | | | |
| 4 | 20 | 150 | ++ | (+) | φ | φ |
| 3 | 45 | 150 | ++ | (+) | φ | φ |
| 5 | 19 | | + | − | φ | φ |
| | | | Ataxy | | | |
| 9 | 33 | | ++ | (+) | φ | φ |
| 7 | 30 | | ++ | (+) | φ | φ |
| 26 | 19 | | ++ | (+) | φ | φ |
| 30 | 32 | | ++ | + | φ | φ |
| 17 | 34 | | ++ | (+) | φ | φ |
| 32 | | | ++ | (+) | φ | φ |
| 29** | | | − | − | φ | φ |
| 28** | | 3800 | − | − | φ | φ |

| Compound of Ex. | Antagonism in the albino mouse of* | | | | | | |
|---|---|---|---|---|---|---|---|
| | Reserpine Preventive ptosis/Sedation | | (2mg/kg sc.) Curative ptosis/Sedation | | Perphenazine catalepsy (10 mg/kg p.o.) | | Tremorine tremor (15 mg/kg i.p.) |
| | $ED_{50}$ | mg/kg | $ED_{50}$ | mg/kg | $ED_{50}$ | mg/kg | $ED_{50}$ mg/kg |
| 19 | 10 | 5 | >50 | 10 | 20 | | 2 |
| 1 | 4 | 3 | >50 | 10 | 3 | | 1 |
| 10 | | | | | | | |
| 4 | 16 | 3 | >50 | 13 | 7 | | 1.5 |
| 3 | 5 | 5 | >50 | 50 | 2 | | 1.0 |
| 5 | 3 | 3 | (+) | (+) | | | φ |
| 9 | 10 | 8 | (+) | 15 | 15 | | 10 |
| 7 | | | | | | | 3 |
| 26 | 25 | 10 | (+) | 10 | 7 | | 5 |
| 30 | 25 | 25 | (+) | φ | 5 | | 5 |
| 17 | 12 | 15 | >25 | ~25 | >25 | | 17 |
| 32 | 10 | 15 | >60 | ~50 | 45 | | 15 |
| 29** | 3^φ 18^φ | φ 100 | | | φ | φ | 50φ |
| 28** | 3^φ 18^φ | φ 300 | | | φ | φ | 50φ |

++ = strong increase
+ = increase
(+) = slight increase
− = decrease
φ = no effect
*drugs administered per os
**administered in doses from 50 to 300 mg/kg

What is claimed is:

1. A neuroleptic or CNS-stimulating medicament composition in dosage form wich contains, as a pharmacologically-active component thereof, an effective concentration of at least one physiologically-acceptable 4,4-diarylpiperidine in admixture with a pharmaceutically-acceptable carrier, and in which at least one physiologically-acceptable 4,4-diarylpiperidine is a member selected from the group consisting of (a) a compound of the formula

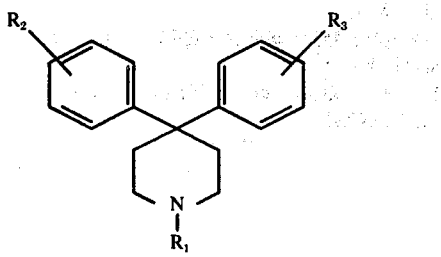

wherein
R₁ is a member selected from the group consisting of —H, alkyl with from 1 to 6 carbon atoms, inclusive, nuclearly-substituted or unsubstituted phen(lower)alkyl, hydroxy(lower)alkyl, (lower)alkyloxo(lower)alkyl, (lower)alkoxy(lower)alkyl, nuclearly-substituted or unsubstituted phenoxy(lower)alkyl, nuclearly-substituted or unsubstituted phenyl(lower)alkoxy(lower)alkyl and nucearly-substituted or unsubstituted phenyloxo(lower)alkyl; each occurrence of "lower" denoting a carbon skeleton having from 1 to 4 carbon atoms, inclusive; and any substituent of a nuclearly-substituted benzene ring being an atom of a halogen having an atomic number from 9 to 35, inclusive; and each of R₃ and R₃ is, independently, a member selected from the group consisting of —H and alkyl having from 1 to 4 carbon atoms, inclusive;

and (b) an acid-addition salt of (a).

2. A composition according to claim 1 wherein R₁ is alkyl having from 1 to 6 carbon atoms, inclusive, hydroxy(lower)alkyl, (lower)alkyloxo(lower)alkyl or (lower)alkoxy(lower)alkyl, and
R₃ is —H.

3. A composition according to claim 2 wherein R₂ is —H.

4. A composition according to claim 3 wherein R₁ is isopropyl.

5. A composition according to claim 1 in unit dosage form, each unit dosage containing from 5 to 70 milligrams of the pharmacologically-active and physiologically-acceptable 4,4-diarylpiperidine.

6. A CNS-stimulating medicament composition according to claim 1 wherein R₂ and R₃ have the meanings ascribed to them in claim 1, and R₁ is a member selected from the group consisting of —H, alkyl with from 1 to 6 carbon atoms, inclusive, nuclearly-substituted or unsubstituted phen(lower)alkyl, hydroxy(lower)alkyl, (lower)alkyloxo(lower)alkyl, (lower)alkoxy(lower)alkyl, nuclearly-substituted or unsubstituted phenoxy(lower)alkyl and nuclearly-substituted or unsubstituted phenyl(lower)alkoxy(lower)alkyl; each occurrence of "lower" denoting a carbon skeleton having from 1 to 4 carbon atoms, inclusive; and any substituent of a nuclearly-substituted benzene ring being an atom of a halogen having an atomic number from 9 to 35, inclusive.

7. A method for stimulating a subject in need of CNS stimulation which comprises administering to the subject an effective amount of medicament composition according to claim 6.

8. A method according to claim 7 wherein the subject is afflicted with a disorder which requires CNS stimulation.

9. A method according to claim 7 which comprises orally administering the 4,4-diarylpiperidine to the subject.

10. A method according to claim 7 wherein R₁ is isopropyl.

11. A CNS-stimulating medicament composition according to claim 1 wherein each of R₂ and R₃ has the meaning ascribed to it in claim 1, and R₁ is —H.

12. A CNS-stimulating medicament composition according to claim 1 wherein each of R₂ and R₃ has the meaning ascribed to it in claim 1, and R₁ is alkyl with from 1 to 6 carbon atoms, inclusive.

13. A CNS-stimulating medicament composition according to claim 1 wherein each of R₂ and R₃ has the meaning ascribed to it in claim 1, and R₁ is nuclearly-substituted or unsubstituted phen(lower)alkyl.

14. A CNS-stimulating medicament composition according to claim 1 wherein each of R₂ and R₃ has the meaning ascribed to it in claim 1, and R₁ is hydroxy(lower)alkyl.

15. A CNS-stimulating medicament composition according to claim 1 wherein each of R₂ and R₃ has the meaning ascribed to it in claim 1, and R₁ is (lower)alkyloxo(lower)alkyl.

16. A CNS-stimulating medicament composition according to claim 1 wherein each of R₂ and R₃ has the meaning ascribed to it in claim 1, and R₁ is (lower)alkoxy(lower)alkyl.

17. A CNS-stimulating medicament composition according to claim 1 wherein each of R₂ and R₃ has the meaning ascribed to it in claim 1, and R₁ is nuclearly-substituted or unsubstituted phenoxy(lower)alkyl.

18. A CNS-stimulating medicament composition according to claim 1 wherein each of R₂ and R₃ has the meaning ascribed to it in claim 1, and R₁ is nuclearly-substituted or unsubstituted phenyl(lower)alkoxy(lower)alkyl.

19. A method which comprises administering to a subject in need of CNS stimulation an effective CNS-stimulating amount of a physiologically-active and therepeutically-acceptable 4,4-diarylpiperidine selected from the group consisting of (a) a compound of the formula

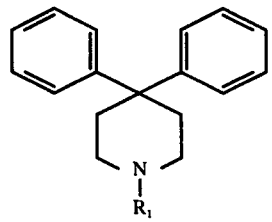

wherein R₁ is a member selected from the group consisting of —H and alkyl with from 1 to 6 carbon atoms,
and (b) an acid-addition salt of (a).

20. A method according to claim 19 for treating neurological disorders of the motoric system of the subject, and disorders being caused by a disturbed regulation of the motoric transmission of said subject requiring improvement of said regulation.

21. A method according to claim 19 for treating a depressive syndrome of a subject afflicted with such syndrome, said subject requiring elevation of depression.

22. A method according to claim 19 for support to the treatment of individuals afflicted with drug addition.

23. A method according to claim 19 wherein the subject is afflicted with a disorder which requires CNS stimulation.

24. A method according to claim 19 wherein $R_1$ is isopropyl.

25. A method according to claim 19 wherein $R_1$ is tertiary butyl.

* * * * *

UNITED STATES PATENT AND TRADEMARK OFFICE
CERTIFICATE OF CORRECTION

PATENT NO. : 4,016,280
DATED : April 5, 1977
INVENTOR(S) : MENGE ET AL.

It is certified that error appears in the above-identified patent and that said Letters Patent are hereby corrected as shown below:

In the Abstract, line 2, "diphenylpiperidine" should read --diphenylpiperidines--; line 6, "acid ad-" should read --acid-ad- --; line 12, "compound" should read --compound,--. Column 1, line 8, "pending" should read --copending--; line 9, "455,041" should read --455,041 (USP 4,022,786)--; line 26, "of the Prior" should read --of Prior--; line 41, "piperidine are" should read --piperidine, are--; line 58, "-dimethylamine" should read -- -dimethylamylamine--; line 59, "-dimethyla-" should read -- -dimethylamyl- --; line 60, "mine" should read --amine--. Column 2, line 1, "-diphenyl-piperidine" should read -- -diphenylpiperidine,--; line 27, "-hydroxyor" should read -- -hydroxy- or--. Column 3, line 21, "(lower)alkoxy-(lower)" should read --(lower)alkoxy(lower)--; in the formula following line 21, "II" should read --II'--; line 55, "CO-group" should read --CO- group--. Column 5, approximately line 4, "CO- group" should read --CO- group--; in the formula bridging columns 5 and 6, "$R_1$" should read --$R_1$ I--; (column 5), line 42, "60" should read --60%--. Column 6, line 7, "1,600,4449" should read --1,600,449--; line 10, "the formulae II or" should read --formulae II and--; line 36, "catalyst" should read --catalyst,--; line 40, "catalyst;" should read --catalyst:--. Column 7, line 32, "acid-solution" should read --acid-addition--; line 40, "water-hydrochloric" should read --water - hydrochloric--; line 41, "inorganic salts" should read --inorganic acids--; line 46, "maleic acids" should read --maleic acid--; line 48, "salicyclic" should read --salicylic--; line 50, "acid addition"

UNITED STATES PATENT AND TRADEMARK OFFICE
CERTIFICATE OF CORRECTION

PATENT NO. : 4,016,280
DATED : April 5, 1977
INVENTOR(S) : MENGE ET AL.

Page 2 of 4

It is certified that error appears in the above-identified patent and that said Letters Patent are hereby corrected as shown below:

should read --acid-addition--; line 58, "Then" should read --Then the 4,4-diphenylpiperidine of formula Ib is reacted with--. Column 8, line 21, "R'" should read --$R_1'$--; line 51, "and" should read --or--. Column 9, line 45, "acid addition" should read --acid-addition--; line 48, "for" should read --of--; line 50, "tataric" should read --tartaric--; line 60, "-methylenebi-" should read -- -methylene-bis- --; line 64, "salicyclic" should read --salicylic--; line 66, "pharmaceutically-accepta-" should read --pharmaceutically accepta- --. Column 10, line 8, "[1 methyl-4,4-" should read --[1-methyl-4,4- --; line 21, "acid addition" should read --acid-addition--; line 30, "ystem" should read --system--; line 32, "acid addition" should read --acid-addition--; line 53, "cuased" should read --caused--; line 55, "formula" should read --formulae--; line 63, "syndroms" should read --syndromes--; line 64, "syndroms" should read --syndromes--. Column 11, line 19, "pharamacologically-" should read --pharmacologically- --; line 20, "acid addition" should read --acid-addition--; line 30, "administrated" should read --administration--. Column 12, line 10, "-diphenylpiperdine" should read -- -diphenylpiperidine--. Column 13, line 22, "acid addition" should read --acid-addition--; line 66, "aluminu" should read --aluminum--. Column 14, line 46, "15" should read --16--; line 47, "pont" should read --point--; line 55, "g" should read --g.--; line 57, "diphenyl-piperidine" should read --diphenylpiperidine--. Column 15, approximately line 33, "1-(teriary" should read --1-(tertiary--. Column 16, line 54, "liqud" should read --liquid--; line 55, "requred" should read --required--; line 60, "is" should read --is a--; line 61, "such" should read

UNITED STATES PATENT AND TRADEMARK OFFICE
CERTIFICATE OF CORRECTION

PATENT NO. : 4,016,280

DATED : April 5, 1977

INVENTOR(S) : MENGE ET AL.

It is certified that error appears in the above-identified patent and that said Letters Patent are hereby corrected as shown below:

--Such--. Column 17, line 23, "1-secondary butyl-" should read --1-(secondary butyl)- --; line 48, "base" should read --base,--; line 55, "hydroxy-piperidine" should read --hydroxypiperidine--. Column 18, line 19, "furmarate" should read --fumarate--; line 30, "hydrochoric" should read --hydrochloric--; line 31, "(3-benzoylpropl)" should read --(3-benzoylpropyl)--; line 37, "(3-Hydroxypropl)" should read --(3-Hydroxypropyl)--; line 50, "phenoxy-(" should read --phenoxy(--; line 51, "lower)alkoxy-(lower)" should read --lower)alkoxy(lower)--; line 54, "fluorobenzoyl-propyl" should read --fluorobenzoylpropyl--; line 66, "addeded" should read --added--, and "60° C" should read --60° to 64° C--. Column 19, line 14, "mm./Hg" should read --mm. Hg--; line 66, "vention" should read --vention.--. Column 20, line 1, "increase of" should read --increase in--; line 3, "sterotypia" should read --stereotypia--; line 5, "tremonin" should read --tremorin--; line 13, "animals" should read --animals;--; line 21, "Stereotype" should read --Stereotypia--; approximately line 48, "$3^h\phi$" should read --$3^h\phi$--; approximately line 49, "$18^h\phi$" should read --$18^h\phi$--; approximately line 50, "$3^h\phi$" should read --$3^h\phi$--; approximately line 51, "$18^h\phi$" should read --$18^h\phi$--; line 61, "wich" should read --which--; line 67, "(a)" should read --a)--. Column 21, line 28, "each of $R_3$" should read --each of $R_2$--; line 31, "(b)" should read --b)--. Column 22, line 41, "therepeutically-" should read

UNITED STATES PATENT AND TRADEMARK OFFICE
CERTIFICATE OF CORRECTION

PATENT NO. : 4,016,280

DATED : April 5, 1977

INVENTOR(S) : MENGE ET AL.

It is certified that error appears in the above-identified patent and that said Letters Patent are hereby corrected as shown below:

--therapeutically- --; line 42, "(a)" should read --a)--; line 59, "(b)" should read --b)--.

Signed and Sealed this

Twenty-seventh Day of June 1978

[SEAL]

Attest:

RUTH C. MASON
Attesting Officer

DONALD W. BANNER
Commissioner of Patents and Trademarks